United States Patent [19]

Barberich et al.

[11] Patent Number: 5,382,591

[45] Date of Patent: Jan. 17, 1995

[54] ANTIPYRETIC AND ANALGESIC METHODS USING OPTICALLY PURE R-KETOROLAC

[75] Inventors: Timothy J. Barberich, Concord; Stephen L. Matson, Harvard, both of Mass.; William J. Wechter, Redlands, Calif.

[73] Assignee: Sepracor Inc., Marlborough, Mass.

[21] Appl. No.: 118,160

[22] Filed: Sep. 8, 1993

Related U.S. Application Data

[63] Continuation of Ser. No. 991,981, Dec. 17, 1992, abandoned.

[51] Int. Cl.⁶ ............................................. A61K 31/40
[52] U.S. Cl. ..................................................... 514/413
[58] Field of Search ......................................... 514/413

[56] References Cited

U.S. PATENT DOCUMENTS 4,089,969 5/1978 Muchowski et al. ............... 548/453

FOREIGN PATENT DOCUMENTS

WO94/13283 5/1994 WIPO .

OTHER PUBLICATIONS

Gusman et al., Chem. Abstracts, CA104(15):129734n, 1986.
Wade, Jr., *Organic Chemistry*, 1987, p. 349.
March, *Advanced Organic Chemistry*, 1977, pp. 108–113.
Brocks et al. "Clinical Pharmacokinetics of Ketorolac Tromethamine" *Clin. Pharmacokinet.* 23(6) 415–427 (1992).
Brune et al. "Aspirin-like Drugs May Block Pain Independently of Prostaglandin Synthesis Inhibition" *Experientia* 47 257–261 (1991).
Buckley et al. "Ketorolac A Review of Its Pharmacodynamic and Pharmacokinetic Properties and Therapeutic Potential" *Drugs* 39(1) 86–109 (1990).
Caldwell et al. "The Metabolic Chiral Inversion and Dispositional Enantioselectivity of the 2-Arylpropionic Acids and Their Biological Consequences" *Biochem. Pharmacol.* 37 (1) 105–114 (1988).
Guzman et al. "Absolute Configuration of (−)-5-Benzoyl-1,2-dihydro-3H-pyrrolo[1,2-a]pyrrole-1-carboxylic Acid, the Active Enantiomer of Ketorolac" *J. Med. Chem.* 29(4) 589–591 (1986).
Jamali et al. "HPLC of Ketorolac Enantiomers and Application to Pharmacokinetics in the Rat" *J. Liquid Chromatogr.* 12(10) 1835–1850 (1989).
Kelley et al. "Ketorolac Prevents Postoperative Small Intestinal Ileus in Rats" *Am. J. of Surgery* 165 107–112 (1993).
Maunuksela et al. "Comparison of Intravenous Ketorolac with Morphine for Postoperative Pain in Children" *Clin. Pharmacol. & Ther.* 52(4) 436–443.
Mroszczak et al. "Pharmacokinetics of (−)S and (+)R Enantiomers of Ketorolac (K) in Humans Following Administration of Racemic Ketorolac Tromethamine (KT)" *Clin. Pharmacol. Ther. PI–13* 126 (1991).
Muchowski et al. "Synthesis and Antiinflammatory and Analgesic Activity of 5-Aroyl-1,2-dihydro-3H-pyrrolo[1,2-a]pyrrole-1-carboxylic Acids and Related Compounds" *J. Med. Chem.* 28(8) 1037–1049 (1985).

(List continued on next page.)

*Primary Examiner*—Raymond J. Henley, III
*Assistant Examiner*—William R. A. Jarvis
*Attorney, Agent, or Firm*—Pennie & Edmonds

[57] ABSTRACT

Methods are disclosed utilizing optically pure R-ketorolac for the treatment of pain, including but not limited to pain associated with toothaches, headaches, sprains, joint pain and surgical pain, for example dental pain (e.g., after periodontal surgery) and ophthalmic pain (e.g., after cataract surgery) while avoiding adverse effects which are associated with the administration of the racemic mixture of ketorolac. The optically pure R-ketorolac is also useful in treating pyrexia while avoiding the adverse effects associated with the administration of the racemic mixture of ketorolac.

12 Claims, No Drawings

OTHER PUBLICATIONS

Muchowski et al., "Synthesis and Antiinflammatory and Analgesic Activity of 5-Aroyl-6-(methylthio)-1,2-dihydro-3H-pyrrolo[1,2-a]pyrrole-1-carboxylic Acids and 1-Methyl-4-(methylthio)-5-aroylpyrrole-2-acetic Acids" *J. Med. Chem.* 32(6) 1202-1207 (1989).

Murray et al. "Nonsteroidal Anti-inflammatory Drugs" *Clin. Pharmacol. (Clin. in Geriatr. Med.)* 6(2) 365-397 (1990).

PJB Publications Ltd. *Scrip's New Product Review No. 51 Ketorolac* (1990).

Rooks et al., "The Analgesic and Anti-inflammatory Profile of Ketorolac and Its Tromethamine Salt" *Drugs Exptl. Clin. Res.* XI(8) 479-492 (1985).

Smith, D. F. *Handbook of Stereoisomers: Therapeutic Drugs* 141 (1989).

Stouten et al., "Comparison of Ketorolac and Morphine for Postoperative Pain After Major Surgery" *Acta Anaesthesiol Scand.* 36 716-721 (1992).

Walker et al. "A Comparative Study of Intramuscular Ketorolac and Pethidine in Labour Pain" *Euro. J. of Obstetrics & Gynecology & Reprod. Bio.* 46 87-94 (1992).

Wong et al. "A Randomized, Double-blind Evaluation of Ketorolac Tromethamine for Postoperative Analgesia in Ambulatory Surgery Patients" *Anesthesiology* 78(1) 6-14 (1993).

Yamaguchi et al. "The Inhibitory Activities of 4580156-S and Its Related Compounds on Prostaglandin Synthetase" *Nippon Yakurigaku Zasshi* 90 295-302 (1987) (with English abstract).

ANTIPYRETIC AND ANALGESIC METHODS USING OPTICALLY PURE R-KETOROLAC

This is a continuation of application(s) Ser. No. 07/991,981 filed on Dec. 17, 1992 now abandoned.

BACKGROUND OF THE INVENTION

This invention relates to novel compositions of matter containing optically pure R-ketorolac. These compositions possess potent activity in treating pain, including but not limited to pain associated with toothaches, headaches, sprains, joint pain and surgical pain, for example dental pain (e.g., after periodontal surgery) and ophthalmic pain (e.g., after cataract surgery) while avoiding adverse effects including but not limited to gastrointestinal, renal and hepatic toxicities, which are associated with the administration of the racemic mixture of ketorolac. Additionally, these novel compositions of matter containing optically pure R-ketorolac are useful in treating or preventing pyrexia while avoiding the adverse effects associated with the administration of the racemic mixture of ketorolac. Also disclosed are methods for treating the above-described conditions in a human while avoiding the adverse effects that are associated with the racemic mixture of ketorolac, by administering the R-isomer of ketorolac to said human.

The active compound of these compositions and methods is an optical isomer of ketorolac. This compound is described in U.S. Pat. No. 4,089,969. Chemically, the active compound is the R-isomer of 5-benzoyl-1,2-dihydro-3H-pyrrolo[1,2-a]pyrrole-1-carboxylic acid, hereinafter referred to as R-ketorolac. The terms "R-isomer of ketorolac" and "R-ketorolac" encompass both the optically pure and the substantially optically pure compositions.

Ketorolac is available commercially only as the 1:1 racemic mixture. That is, it is available only as a mixture of optical isomers, called enantiomers.

Steric Relationship and Drug Action

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they are mirror images of one another. A specific stereoisomer may also be referred to as an enantiomer, and a mixture of such isomers is often called an enantiomeric or racemic mixture.

Stereochemical purity is of importance in the field of pharmaceuticals, where 12 of the 20 most prescribed drugs exhibit chirality. A case in point is provided by the L-form of the beta-adrenergic blocking agent, propranolol, which is known to be 100 times more potent than the D-enantiomer.

Furthermore, optical purity is important since certain isomers may actually be deleterious rather than simply inert. For example, it has been suggested that the D-enantiomer of thalidomide was a safe and effective sedative when prescribed for the control of morning sickness during pregnancy, while the corresponding L-enantiomer has been believed to be a potent teratogen.

Ketorolac is a member of a class of compounds known as nonsteroidal anti-inflammatory agents (NSAIDs). As a class of agents, NSAIDs exhibit analgesic, anti-inflammatory, and antipyretic activity. The class includes well known commercial pain relievers such as ibuprofen and aspirin. The NSAID of the present invention is drawn from the 2-arylpropionic acids. Ketorolac, like other aryl alkanoic acids, is known to inhibit the biosynthesis of prostaglandins by the inhibition of the cyclo-oxygenase enzyme which is ubiquitous in mammalian tissues. See Buckley et al., *Drugs,* 39(1):86–109 (1990).

The synthesis of racemic ketorolac is disclosed in Muchowski et al., *J. Med. Chem.,* 28(8):1037–1049 (1985). The enantiomers of ketorolac are disclosed in Guzman et al., *J. Med. Chem.,* 29(4):589–591 (1986). This reference alleges that the pharmacological effects of ketorolac are almost entirely due to the S(−)enantiomer.

Pharmacokinetic studies in the rat suggest no in vivo inversion of the enantiomers of ketorolac. See Jamali et al., *J. Liquid Chromatogr.,* 12(10):1835–1850 (1989). The pharmacokinetic profiles of the enantiomers of ketorolac in man indicate that the S-enantiomer may be more rapidly excreted or metabolized than the R-enantiomer. See Mroszczak et al., *Clin. Pharmacol. Ther.,* PI-13, p.126 (February 1991).

The enantiomers of several 2-arylpropionic acids are disclosed in Yamaguchi et al., *Nippon Yakurigaku Zasshi.* 90:295–302 (1987). This reference states that the S-enantiomers of 2-arylpropionic acids have 15–300 times higher prostaglandin synthetase inhibitory activities than the R-enantiomers in the rat.

Caldwell et al., *Biochem. Pharmacol.,* 37: 105–114 (1988) allege that "at best, the R-isomers [of aryl alkanoic acids] function as prodrugs for the therapeutically active S-forms" when the racemic drug is administered and add to both the therapeutic and toxic effects of the active S-enantiomers. This reference further contends that, "at worst, the R-enantiomers are undesirable impurities in the active drug" causing difficulties due to non-stereoselective toxicity and further alleges that the use of the S-isomers should provide safer and more effective use of this class of drugs.

The racemic mixture of ketorolac is presently used primarily as an analgesic agent in treating pain, including but not limited to pain associated with toothaches, headaches, sprains, joint pain and surgical pain, for example dental pain (e.g., after periodontal surgery) and ophthalmic pain (e.g., after cataract surgery).

Pain is a common symptom, reflecting either physical (i.e., the result of tissue injury or inflammation) or emotional discomfort. Pain is a complex subjective phenomenon comprised of a sensation reflecting real or potential tissue damage, and the affective response this generates. Pain may be classified as either acute or chronic, and it is of a variety of particular types. Acute pain is an essential biologic signal of the potential for, or the extent of tissue injury. In contrast, chronic pain is physically and psychologically debilitating, and it no longer serves its adaptive biologic role. In many patients, organic disease may be insufficient to explain the degree of pain. Chronic pain may be associated with conditions including but not limited to osteoarthritis, rheumatoid arthritis, soft tissue pain syndromes, and headaches.

Pyrexia, or fever, is an elevation in body temperature as a result of infection, tissue damage, inflammation, graft rejection, malignancy or other disease states. The regulation of body temperature requires a delicate balance between the production and loss of heat. The hypothalamus regulates the target point at which body temperature is maintained. In fever, this target point is elevated and antipyretic compositions promote its return to a normal level.

Many of the NSAIDs cause somewhat similar adverse effects. These adverse effects include but are not limited to gastrointestinal, renal and hepatic toxicities. The administration of the racemic mixture of ketorolac has been found to cause these toxicities, as well as other adverse effects. These other adverse effects include but are not limited to nausea, somnolence, headache, dizziness, pruritis, increased sweating, increases in bleeding times due to disruption of platelet function, and prolongation of gestation due to uterine effects.

Thus, it would be particularly desirable to find a compound with the advantages of the racemic mixture of ketorolac which would not have the aforementioned disadvantages.

SUMMARY OF THE INVENTION

It has now been discovered that the optically pure R-isomer of ketorolac is an effective analgesic that avoids adverse effects which are associated with the administration of the racemic mixture of ketorolac. These adverse effects include but are not limited to gastrointestinal, renal and hepatic toxicities, nausea, somnolence, headache, dizziness, pruritis, increased sweating, increases in bleeding times, and prolongation of gestation. The present invention is also based in part on the discovery that these novel compositions of matter containing the optically pure R-isomer of ketorolac are useful in treating or preventing pyrexia while avoiding the above-described adverse effects associated with the administration of racemic ketorolac. The present invention also includes methods for treating the above-described conditions in a human while avoiding the adverse effects that are associated with the racemic mixture of ketorolac by administering the optically pure R-isomer of ketorolac to said human.

DETAILED DESCRIPTION OF THE INVENTION

The present invention encompasses a method of eliciting an analgesic effect in a human, while avoiding the concomitant liability of adverse effects associated with the administration of racemic ketorolac, which comprises administering to a human in need of analgesic therapy, an amount of R-ketorolac, or a pharmaceutically acceptable salt thereof, substantially free of the S-stereoisomer, said amount being sufficient to alleviate pain, but insufficient to cause the adverse effects associated with the administration of the racemic mixture of ketorolac.

The present invention also encompasses an analgesic composition for the treatment of a human in need of analgesic therapy, which comprises an amount of R-ketorolac or a pharmaceutically acceptable salt thereof, substantially free of the S-stereoisomer, said amount being sufficient to alleviate pain but insufficient to cause the adverse effects associated with the racemic mixture.

The present invention further encompasses a method of treating or preventing pyrexia in a human, while avoiding the concomitant liability of adverse effects associated with the administration of racemic ketorolac, which comprises administering to a human in need of such therapy an amount of R-ketorolac or a pharmaceutically acceptable salt thereof, substantially free of the S-stereoisomer, said amount being sufficient to alleviate or prevent said pyrexia but insufficient to cause adverse effects associated with the administration of the racemic mixture of ketorolac.

In addition, the present invention encompasses an antipyretic composition for the treatment of a human in need of such therapy which comprises an amount of R-ketorolac or a pharmaceutically acceptable salt thereof, substantially free of the S-stereoisomer, said amount being sufficient to alleviate or prevent pyrexia but insufficient to cause adverse effects associated with the administration of racemic ketorolac.

The available racemic mixture of ketorolac (i.e., a 1:1 mixture of the two enantiomers) possesses analgesic and antipyretic activity; however, this commercially available drug, while offering the expectation of efficacy, causes adverse effects. Utilizing the substantially optically pure R-isomer of ketorolac results in clearer dose related definitions of efficacy, diminished adverse effects, and accordingly, an improved therapeutic index. It is therefore more desirable to use the R-isomer of ketorolac than the racemic mixture.

The term "adverse effects" includes, but is not limited to gastrointestinal, renal and hepatic toxicities, nausea, somnolence, headache, dizziness, pruritis, increased sweating, increases in bleeding times, and prolongation of gestation. The term "gastrointestinal toxicities" includes but is not limited to gastric and intestinal ulcerations and erosions. The term "renal toxicities" includes but is not limited to such conditions as papillary necrosis and chronic interstitial nephritis.

The term "substantially free of the Sstereoisomer" as used herein means that the compositions contain a greater proportion of the R-isomer of ketorolac in relation to the S-isomer of ketorolac. In a preferred embodiment the term "substantially free of the S-isomer" as used herein means that the composition contains at least 90% by weight of an R-ketorolac and 10% by weight or less of S-ketorolac. In a preferred embodiment the term "substantially free of the S-stereoisomer" means that the composition contains at least 99% by weight of R-ketorolac and 1% or less of the S-ketorolac. In the most preferred embodiment, the term "substantially free of the S-stereoisomer" as used herein means that the composition contains greater than 99% by weight of R-ketorolac. These percentages are based upon the total amount of ketorolac present in the composition. The phrases "substantially optically pure R-isomer of ketorolac" or "substantially optically pure R-ketorolac" and "optically pure R-isomer of ketorolac" or "optically pure R-ketorolac" are also encompassed by the above-described amounts.

The term "eliciting an analgesic effect" as used herein means treating, relieving, ameliorating or preventing mild to moderate pain. For example, such pain includes but is not limited to pain associated with toothaches, headaches, sprains, joint pain, surgical pain, dental pain (e.g., after periodontal surgery) and ophthalmic pain (e.g., after cataract surgery).

The term "pyrexia" as used herein means the elevation of body temperature brought about by infectious disease, tissue damage, inflammation, graft rejection, malignancy or other disease states.

The magnitude of a prophylactic or therapeutic dose of R-ketorolac in the acute or chronic management of disease will vary with the severity of the condition to be treated, and the route of administration. The dose, and perhaps the dose frequency, will also vary according to the age, body weight, and response of the individual patient. In general, the total daily dose range for R-ketorolac, for the conditions described herein, is from about 15 mg to about 500 mg, in single or divided doses. Preferably, a daily dose range should be between about 30 mg to about 250 mg, in single or divided doses. In managing the patient, the therapy should be initiated at a lower dose and increased depending on the patient's global response. It is further recommended that infants, children, patients over 65 years, and those with impaired renal or hepatic function initially receive lower doses, and that they be titrated based on global response and blood level. It may be necessary to use dosages outside these ranges in some cases. Further, it is noted that the clinician or treating physician will know how and when to interrupt, adjust or terminate therapy in conjunction with individual patient response.

The terms "an amount sufficient to alleviate pain but insufficient to cause said adverse effects" and "an amount sufficient to alleviate or prevent said pyrexia but insufficient to cause said adverse effects" are encompassed by the above-described dosage amounts and dose frequency schedule.

Any suitable route of administration may be employed for providing the patient with an effective dosage of R-ketorolac. For example, oral, rectal, parenteral (subcutaneous, intravenous, intramuscular), intrathecal, transdermal, and like forms of administration may be employed. Dosage forms include tablets, troches, dispersions, suspensions, solutions, capsules, patches, and the like. A preferred form of administration is intramuscular injection.

The pharmaceutical compositions of the present invention comprise R-ketorolac as the active ingredient, or a pharmaceutically acceptable salt thereof, and may also contain a pharmaceutically acceptable carrier, and optionally, other therapeutic ingredients.

The term "pharmaceutically acceptable salt" refers to salts prepared from pharmaceutically acceptable non-toxic acids or bases including inorganic acids and bases and organic acids and bases. Since the compounds of the present invention are acidic, salts may be prepared from pharmaceutically acceptable non-toxic bases including inorganic and organic bases. Suitable pharmaceutically acceptable base addition salts for the compounds of the present invention include metallic salts made from aluminum, calcium, lithium, magnesium, potassium, sodium and zinc or organic salts made from N,N'-dibenzylethylenediamine, chloroprocaine, choline, lysine, diethanolamine, ethylenediamine, meglumine (N-methylglucamine) and procaine.

The compositions of the present invention include compositions such as suspensions, solutions, and elixirs; aerosols; or carriers such as starches, sugars, microcrystalline cellulose, diluents, granulating agents, lubricants, binders, disintegrating agents and the like, in the case of oral solid preparations (such as, powders, capsules, and tablets).

In addition to the common dosage forms set out above, the compounds of the present invention may also be administered by controlled release means and/or delivery devices such as those described in U.S. Pat. Nos. 3,845,770; 3,916,899; 3,536,809; 3,598,123; and 4,008,719, the disclosures of which are hereby incorporated by reference.

Pharmaceutical compositions of the present invention suitable for oral administration may be presented as discrete units such as capsules, cachets, or tablets, or aerosol sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent.

The invention is further defined by reference to the following examples describing in detail the compositions of the present invention as well as their utility. It will be apparent to those skilled in the art that many modifications, both to materials and methods, may be practiced without departing from the purpose and interest of this invention.

EXAMPLES

Example 1

The antiphenylquinone writhing test is a standard procedure for detecting and comparing analgesic activity and generally correlates well with human efficacy.

Mice are first dosed with the medications studied. The medications used are two dose levels of R(+) ketorolac and two dose levels of racemic ketorolac. The mice are then challenged with phenyl-p-benzoquinone given intraperitoneally and observed for the characteristic stretch-writhing syndrome. Lack of writhing constitutes a positive response. The degree of analgesic protection can be calculated on the basis of suppression of writhing relative to control animals run the same day. Time response data are also obtained. Observations are made early enough post-dosing to detect differences in onset.

Example 2

Toxicity

The following is a description of a thirty day general toxicology study of the effects of the isomers of ketorolac in the rat. Groups of 6–10 rats are injected with either vehicle, racemic ketorolac (30, 15, 5 and 1 mg/kg/day), S-ketorolac (30, 15, 5 and 1 mg/kg/day) and R-ketorolac (30, 15, 5 and 1 mg/kg/day). During the first 24 hours after the first dose, 24 hour urine samples and blood samples are collected from all eight groups to determine the levels of serum sodium, creatine, blood urea nitrogen, liver transaminases (ALT and AST) and urine creatine. These measurements are repeated on days 15 and 30 of treatment. Clinical observations are made daily and body weights are determined on days 1, 15, 22, and 29. At necropsy, gross abnormalities are recorded, with particular attention to the GI tract above the large colon. The entire length is opened, washed, and all lesions are scored and counted. The kidneys are mounted for histological evaluation by light microscopy.

What is claimed is:

1. A method of eliciting an analgesic effect with reduced gastrointestinal toxicity in a human, comprising administering to said human a therapeutically effective analgesic amount of R-ketorolac, or a pharmaceutically acceptable salt thereof, substantially free of its S-stereoisomer.

2. The method of claim 1 wherein said R-ketorolac or a pharmaceutically acceptable salt thereof is administered by intrathecal or intravenous infusion, intramuscular injection, or transdermal delivery.

3. The method of claim 2 wherein the amount of R-ketorolac or a pharmaceutically acceptable salt thereof administered is from about 15 mg to about 500 mg per day.

4. The method of claim 3 wherein the amount administered is from about 30 mg to about 250 mg per day.

5. The method of claim 1 wherein the amount of said R-ketorolac or a pharmaceutically acceptable salt thereof is greater than approximately 90% by weight of the total weight of ketorolac.

6. The method of claim 1 wherein the amount of said R-ketorolac or a pharmaceutically acceptable salt thereof, substantially free of the S-stereoisomer, is administered together with a pharmaceutically acceptable carrier.

7. A method of treating pyrexia with reduced gastrointestinal toxicity in a human, comprising administering to said human a therapeutically effective antipyretic amount of R-ketorolac or a pharmaceutically acceptable salt thereof, substantially free of its S-stereoisomer.

8. The method of claim 7 wherein said R-ketorolac or a pharmaceutically acceptable salt thereof is administered by intrathecal or intravenous infusion, intramuscular injection, or transdermal delivery.

9. The method of claim 8 wherein the amount of R-ketorolac or a pharmaceutically acceptable salt thereof administered is from about 15 mg to about 500 mg per day.

10. The method of claim 9 wherein the amount administered is from about 30 mg to about 250 mg per day.

11. The method of claim 7 wherein the amount of said R-ketorolac or a pharmaceutically acceptable salt thereof is greater than approximately 90% by weight of the total weight of ketorolac.

12. The method of claim 7 wherein the amount of said R-ketorolac or a pharmaceutically acceptable salt thereof, substantially free of the S-stereoisomer, is administered together with a pharmaceutically acceptable carrier.

* * * * *